United States Patent
Henry et al.

(10) Patent No.: US 6,764,563 B2
(45) Date of Patent: *Jul. 20, 2004

(54) REGISTRATION SYSTEM FOR PHASING SIMULTANEOUSLY ADVANCING WEBS OF MATERIAL HAVING VARIABLE PITCH LENGTHS

(75) Inventors: Douglass Scott Henry, West Chester, OH (US); Michael S. Kolodesh, Loveland, OH (US); Charles Phillip Miller, Cincinnati, OH (US); Toshiyuki Matsuda, Hyougo (JP); Alton Henry Stephens, West Chester, OH (US); Paul Kevin King, II, Overland Park, KS (US)

(73) Assignee: The Procter & Gamble Company, Cincinnati, OH (US)

( * ) Notice: Subject to any disclaimer, the term of this patent is extended or adjusted under 35 U.S.C. 154(b) by 55 days.

This patent is subject to a terminal disclaimer.

(21) Appl. No.: 10/161,360
(22) Filed: Jun. 3, 2002

(65) Prior Publication Data
US 2003/0010455 A1 Jan. 16, 2003

Related U.S. Application Data

(63) Continuation-in-part of application No. 09/495,651, filed on Feb. 1, 2000, now Pat. No. 6,444,064, which is a continuation-in-part of application No. PCT/US98/27135, filed on Dec. 19, 1998.

(30) Foreign Application Priority Data

Dec. 19, 1997 (WO) ............................... PCT/US97/23620

(51) Int. Cl.⁷ .................. B32B 31/00; B65H 23/00; B65H 77/00
(52) U.S. Cl. .................. 156/64; 156/229; 156/324; 156/378; 226/29; 700/124; 700/125
(58) Field of Search .................. 156/64, 229, 324, 156/351, 361, 350, 362, 378, 494; 226/28, 29, 30, 27; 700/125, 124, 122

(56) References Cited

U.S. PATENT DOCUMENTS 4,540,595 A   9/1985   Acitelli et al.
4,549,917 A   10/1985  Jensen, Jr.

(List continued on next page.)

FOREIGN PATENT DOCUMENTS

| WO | WO 96/29966 A1 | 10/1996 |
| WO | WO 97/24094 A1 | 7/1997 |
| WO | WO 97/24283 A1 | 7/1997 |
| WO | WO 00/40196 A1 | 7/2000 |
| WO | WO 00/59428 A1 | 10/2000 |
| WO | WO 00/59429 A1 | 10/2000 |

*Primary Examiner*—Sue A. Purvis
(74) *Attorney, Agent, or Firm*—Jack L. Oney, Jr.; Michael S. Kolodesh; Jay A. Krebs

(57) ABSTRACT

Disclosed is a registration system and a method useful for controlling and correcting the phase and position of simultaneously advancing webs having pre-printed objects spaced at a pitch length characterized by a pitch variation to a target web. Also disclosed are consumer products, such as disposable absorbent articles including the preprinted objects which were previously included in the webs phased before combining with a target web by utilizing the instant registration system. The pre-printed objects may include pre-printed, pre-bonded, pre-applied, pre-cut, or pre-glued objects or elements of disposable absorbent articles or registration marks produced on a separate independent process not control-linked to the instant registration method. The registration marks may be visible or normally invisible to the human eye.

13 Claims, 7 Drawing Sheets

U.S. PATENT DOCUMENTS

| | | |
|---|---|---|
| 4,680,205 A | 7/1987 | Lerner et al. |
| 4,695,278 A | 9/1987 | Lawson |
| 4,795,454 A | 1/1989 | Dragoo |
| 4,795,513 A * | 1/1989 | Jensen, Jr. ............... 156/108 |
| 4,837,715 A | 6/1989 | Ungpiyakul et al. |
| 5,045,135 A | 9/1991 | Meissner et al. |
| 5,094,708 A | 3/1992 | Bechtel et al. |
| 5,221,058 A | 6/1993 | Fillis |
| 5,235,515 A | 8/1993 | Ungpiyakul et al. |
| 5,286,543 A | 2/1994 | Ungpiyakul et al. |
| 5,359,525 A | 10/1994 | Weyenberg |
| 5,483,893 A | 1/1996 | Isaac et al. |
| 5,569,234 A | 10/1996 | Buell et al. |
| 5,665,151 A | 9/1997 | Escano et al. |
| 5,722,178 A | 3/1998 | Wells |
| 5,766,389 A | 6/1998 | Brandon et al. |
| 5,932,039 A | 8/1999 | Popp et al. |
| 5,964,970 A | 10/1999 | Woolwine et al. |
| 5,980,087 A | 11/1999 | Brandon et al. |
| 6,033,502 A | 3/2000 | Coenen et al. |
| 6,074,333 A | 6/2000 | Rajala et al. |
| 6,245,168 B1 | 6/2001 | Coenen et al. |
| 6,404,910 B1 | 6/2002 | Ungpiyakul et al. |

* cited by examiner

REGISTRATION SYSTEM FOR PHASING SIMULTANEOUSLY ADVANCING WEBS OF MATERIAL HAVING VARIABLE PITCH LENGTHS

This application is a continuation-in-part of the parent application U.S. Ser. No. 09/495,651 filed Feb. 1, 2000, now U.S. Pat. No. 6,444,064 B1, which is a continuation-in-part of PCT/US98/27135 filed Dec. 19, 1998.

FIELD OF THE INVENTION

The present invention relates to a registration system and to a method for phasing simultaneously advancing webs of materials, carrying pre-fabricated elements consecutively spaced at pitch lengths having small but significant variation, to a target web. Further, the present invention relates to consumer products, such as disposable absorbent articles, that may include an element or a registration mark which was included in the continuous webs before phasing with the target web in the process of making disposable absorbent articles by utilizing the instant registration system.

BACKGROUND OF THE INVENTION

In the manufacture of disposable absorbent articles such as diapers and catamenials, it is a common manufacturing practice to combine continuously moving webs. These webs are typically represented by plastic films, non-wovens, elastics, etc. supplied to a converting line in their original production form and do not require special positioning before combining with other materials. However, the manufacture of disposable absorbent articles may benefit if the above materials are supplied to the converting line as prefabricated materials, i.e., produced off the converting line and carrying various elements of disposable absorbent articles consecutively spaced along the web length at a nominal pitch length determined by the length of a particular absorbent article. Because the pitch length between the consecutively spaced elements of the prefabricated materials can vary at small but significant variations, in order to ensure consistent positioning of the product elements in every absorbent article, there is a demand for a method to phase or register the consecutively spaced prefabricated elements to desired positions on a target web before combining the prefabricated materials with the target web into a final article or product.

The pre-fabricated elements may include preprinted registered graphic designs or characters that are desirably used in connection with disposable articles such as diapers to enhance their outward appearance for greater consumer acceptance. The positioning of a web preprinted with registered graphics such that the graphics are properly placed in relation to the rest of the diaper product is desirable, e.g., in order to provide a large-sized graphic without cutting it at an incorrect location, has been typically problematic. This is important not only for desirable aesthetic appearance, but also for example, because young children may become disturbed at seeing graphic representations of animals cut up into pieces (e.g., a head cut off).

In addition, breathable polymer films that are particularly useful as backsheet materials for disposable absorbent articles typically have good surface characteristics that make them suitable for the application of multi-colored, high resolution graphics, but such films tend to be mechanically unstable with a particular tendency toward thermal shrinkage in the machine direction. Such instabilities contribute to the difficulty in correctly positioning the pre-printed polymer web on the product web such that the graphic is correctly positioned, or phased, to the product web.

Various methods and apparatus have previously been used for combining such components in a desired relationship. For example, in conventional "discrete phasing" operations, the product is built around the printed graphic, by adjusting the timing position of the machinery in response to a correction signal. However, it cannot be used in operations where more than one web bearing a preprinted (or other phased object) is required for the process, since the machinery can move in response to the graphics on one web only. See, e.g., International Publication No. WO 96/29966.

In "non-continuous web placement" operations, the graphic-printed web is discretized, or cut, into segments. Each segment is then placed on the target web or product in the desired position. This does not, however, ensure the centering of the graphic on the target web; furthermore, it limits the overall product design. The length of the discretized segments must be less than the length of the product, which may allow leakage in the areas where the product is longer than the discretized segment, for example, in the waist region of a diaper.

Other control systems and apparatus for registration have been described, see International Publications WO 97/24094 and WO 97/24283. However, the existing systems or apparatus for registration addresses a system in which inherent significant material instabilities exist, nor do they address a system in which the pitch length of the preprinted graphic is non-uniform, particularly if the preprinted pitch length is longer than the pitch length of the product under production. Similarly, a control system such as that disclosed in U.S. Pat. No. 5,766,389 requires a fixed target pitch. In practice, the target pitch can be subject to the same instabilities as that of the registered printing.

Based on the foregoing, there is a need for a registration system for phasing simultaneously advancing webs having variable pitch lengths, at least one of which has consecutively spaced prefabricated objects (e.g., registered graphics), and the other of which (e.g., a diaper product web) contains consecutively spaced target objects (e.g., absorbent cores). Furthermore, there is a need for a registration control system that can account for the material specific instabilities that inherently exist in such webs and that present small but significant variations resulting therefrom, which make it difficult to combine such webs. In addition, there is a need for a system in which registration of incoming webs having either longer or shorter pitch lengths than the pitch length of the product under production is possible. None of the existing systems provides all of the advantages and benefits of the present invention.

SUMMARY OF THE INVENTION

The present invention is directed to a registration system for phasing simultaneously advancing webs of material having variable pitch lengths comprising: (a) means for feeding a continuous target web containing consecutively spaced target objects along a path at a first velocity, the target web having a target web pitch length between consecutive target objects; (b) means for feeding a continuous controlled web of material preprinted with consecutively spaced preprinted objects along a path at a second velocity, the preprinted web having a controlled web pitch length between consecutive preprinted objects; (c) detection means for detecting the preprinted objects of the controlled web by sensing by an optic that electronically strobes a resolver providing actual position data; (d) means for generating an error signal based upon the detection of the preprinted objects of the controlled web and comparing to affixed target position constant; (e) means for adjusting the controlled web pitch length such that the controlled web pitch length is approximately equal to the target web pitch length to maintain registration due to pitch mismatch; and (f) means for adjusting the second velocity such that the preprinted objects are shifted toward the target objects on the target web, wherein the controlled web pitch length is greater than the target pitch length to pucker the controlled web to provide desired visual and tactile properties to a finished product, and wherein the controlled web has a puckering level +/−2% or greater.

In other aspects of the invention, the target web pitch length is greater than the controlled pitch length to pucker the target web to provide desired visual and tactile properties to a finished product, wherein the target web has a puckering level +/−2% or greater.

Still in other aspects of the invention the puckering levels of the controlled web or the target web can be+/−5%, +/−10%, +/−20%, or +/−50% and greater.

These and other features, aspects, and advantages of the invention will become evident to those skilled in the art from a reading of the present disclosure.

BRIEF DESCRIPTION OF THE DRAWINGS

While the specification concludes with claims particularly pointing out and distinctly claiming the invention, it is believed that the present invention will be better understood from the following description which is taken in conjunction with the accompanying drawings, in which like designations are used to designate substantially identical elements, and in which:

DETAILED DESCRIPTION OF THE INVENTION

All references cited herein are incorporated herein by reference in their entireties. Citation of any reference is not an admission regarding any determination as to its availability as prior art to the claimed invention.

As used herein, the following terms are defined as follows.

Figure 1:
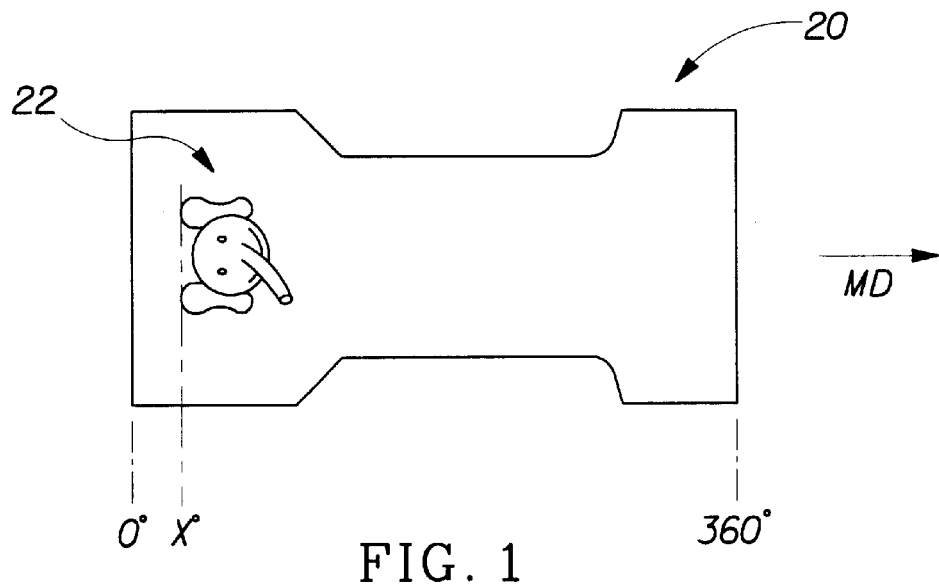
FIG. 1 is a plan view of a preferred embodiment of a disposable diaper of the present invention in a flat, uncontracted position showing a desired location for a preprinted graphic object.
Figure 5:
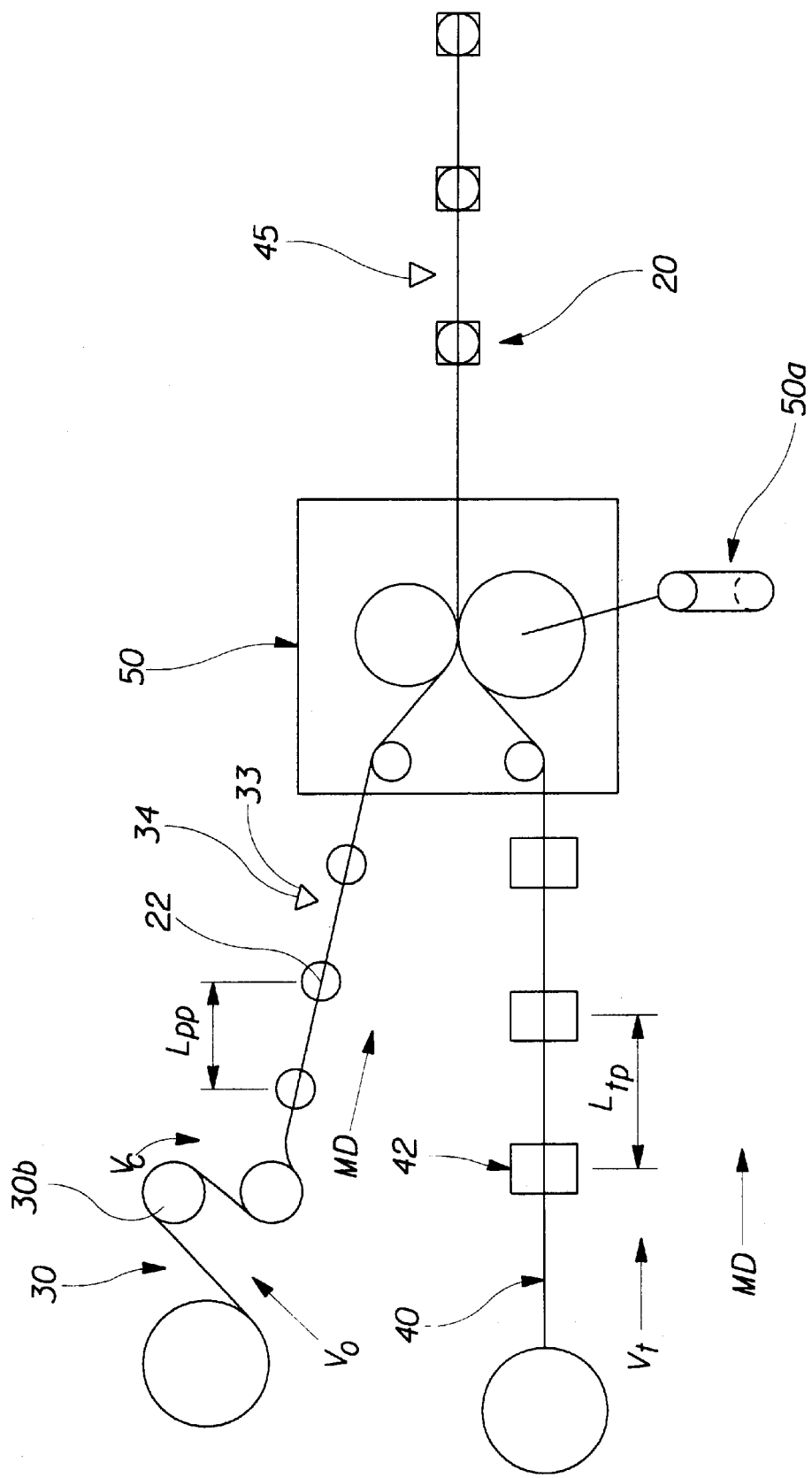
FIG. 5 is a schematic diagram showing the process of combining two simultaneously advancing webs.

"Machine direction" or "MD" means the direction of movement of the product along a manufacturing line. The machine direction is shown in FIGS. 1 and 5 as an arrow labeled MD.

"Phase" refers to the machine direction position of an object expressed as a degree of rotation. For example, the phase representation from 0° to 360° for a flat, uncontracted diaper 20 is shown in FIG. 1. The phase position of an object can be described as any identifiable feature of the object. In FIG. 1, X° is representative of an exemplary desired phase position of the graphic object 22.

"Product pitch length" means the length of material, on a relaxed basis, that runs the full length of the product under production. A product pitch for typical diaper products is illustrated as "PP" in FIG. 2B.

"Registered process" means that two or more continuous webs having phased features are combined in a correct phase relationship to one another.

"Registered graphics" refers to single or multiple color graphic objects that are printed on a web close to a specified pitch length on a relaxed web basis. The registration system of the present invention permits small but significant variation from the intended product pitch length of the product delivered.

"Target web" or "independent web" is the main web which represents the product under production. This target web may be a diaper chassis with the leading edge of the absorbent core being a reference for the target object. It is to be expected that this reference target object may also have a spacing with small but significant variations. In typical use of the present invention an arbitrary once per product "strobe" is used as the reference. Small but significant variation in strobe locus relative to the passing of the reference target object is to be expected.

"Target object" means the location on the target web to which the preprinted object on the controlled web is intended to align. Note that alignment may take place at some standard offset from a easily recognizable feature or "target object."

"Target web pitch length" means the nominal repeat length between consecutively spaced target objects on the target web. The target web pitch length may contain small but significant variation during the use of the registration system of the present invention, e.g., ±2% between consecutive target objects.

"Controlled web" or "manipulated web" means the preprinted web which is manipulated (extended or contracted) as needed to align the preprinted object with the target object. Preferably, the controlled web is comprised of a microporous polymer film suitable for use as, or as part of, a diaper backsheet.

"Preprinted object" means the prefabricated object produced off or on the converting line on a separate independent process not control-linked to the registration process and located on the controlled web at consecutively spaced, but typically not statistically controllable, locations on the controlled web. The term "preprinted object" as used herein may refer to preprinted, pre-bonded, pre-applied, pre-cut, pre-glued, and other objects or elements or a collection of objects (for example, graphics 122 in FIG. 8) of disposable absorbent articles. Furthermore, the term "preprinted object"

also refers to registration marks to be used in the registration process; the registration marks may be both visible and normally invisible to the human eye. The invisible mark cannot be differentiated by the human eye between the color of the preprinted object and the carrier web.

"Controlled web pitch length" means the repeat length between consecutively spaced preprinted objects on the controlled web. Like the target web pitch length, the controlled web pitch length may contain small but significant variation during the use of the registration system of the present invention.

One embodiment of the present invention is directed to a registration process for phasing simultaneously advancing continuous target and controlled webs, the target web containing target objects and the controlled web containing preprinted objects, while permitting all in-running continuous webs to sustain small but significant variations in the spacing of key objects (such as preprinted graphics). Such variations may result, for example, from virtual impossibility to maintain a constant web tension during preprinting (due to machine variations) and then in a roll form (due to inherent tension differential among web layers of the roll), as well as climatic conditions affecting, for example, mechanically unstable microporous polymer films during storage.

It is noted that any other polymer films, non-woven or woven webs, etc. capable of stretching under a tension force applied along the web path, can be useful as controlled webs herein. It is also noted that although the description of embodiments contained herein is primarily given in the context of a diaper converting line, i.e., registration of preprinted objects phased to diaper cores (target objects) on a diaper converting line, it will be understood by those of skill in the art that the registration process herein may be used to phase multiple simultaneously fed webs in any application.

In conventional unit operation registration processes, the position of only a single phased web must be considered. The phase of the unit operation is advanced or retarded as needed to place the function of the unit operation in correct phase relationship to the single phased web. Such a system cannot be used, however, to combine two or more incoming webs in correct phase, as the preprinted pitch lengths of the target and preprinted objects on each will rarely be identical.

Where two or more webs each carrying phased objects must be combined in a predetermined relationship, information pertaining to the phase position of the target web, usually the product under production, e.g., the diaper chassis assembly, must be fed to the web handling process. In addition, the position of the phased objects (e.g., a preprinted object, such as a preprinted graphic or a registration mark on a polymer backsheet web or a non-woven topsheet) on each incoming, controlled web which is to be combined with the target web must also be known and fed. As previously noted, the target web pitch length and the controlled web pitch length are rarely identical. It will be understood by those of skill in the art that any incoming fed web may be designated as a target web or a controlled web, and processed accordingly.

The continuous registration system of the present invention performs two functions simultaneously in order to correctly combine two or more incoming webs having different phase positions, as described above. First, it continuously corrects the preprinted pitch length, or spacing of the graphics consecutively preprinted on the controlled web, to match the pitch length of the target web. Second, it continuously synchronizes the phase positions of the two webs such that they are combined in the proper position, e.g., such that the graphic 22 is correctly located as desired on the diaper 20, for example, in substantially the positions shown in FIGS. 1, 7 or 8.

Figure 2A:
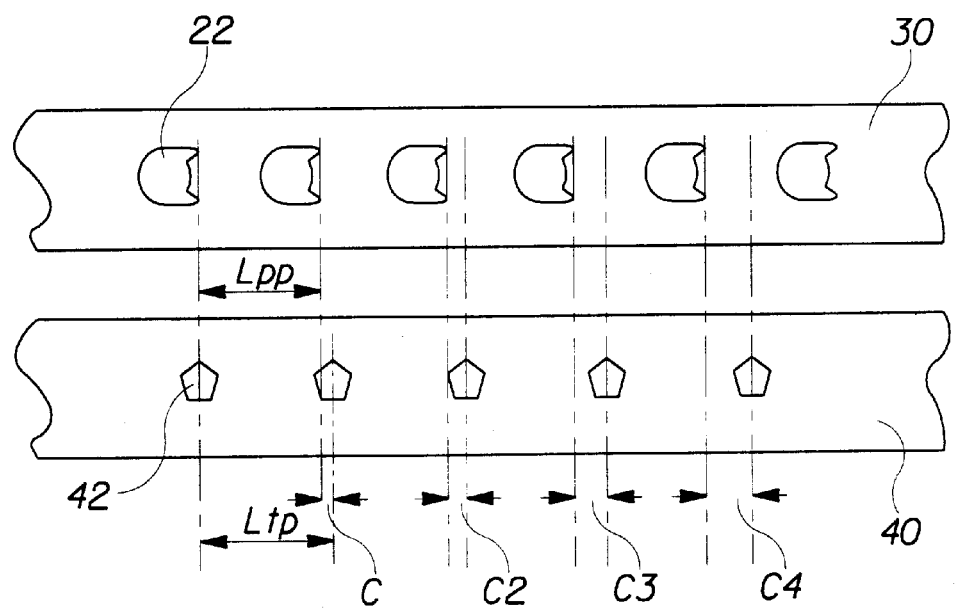
FIG. 2A is a schematic diagram showing simplified representations of a portion of a continuous diaper backsheet web having consecutively spaced graphics printed thereon and a portion of a diaper product web.
Figure 2B:
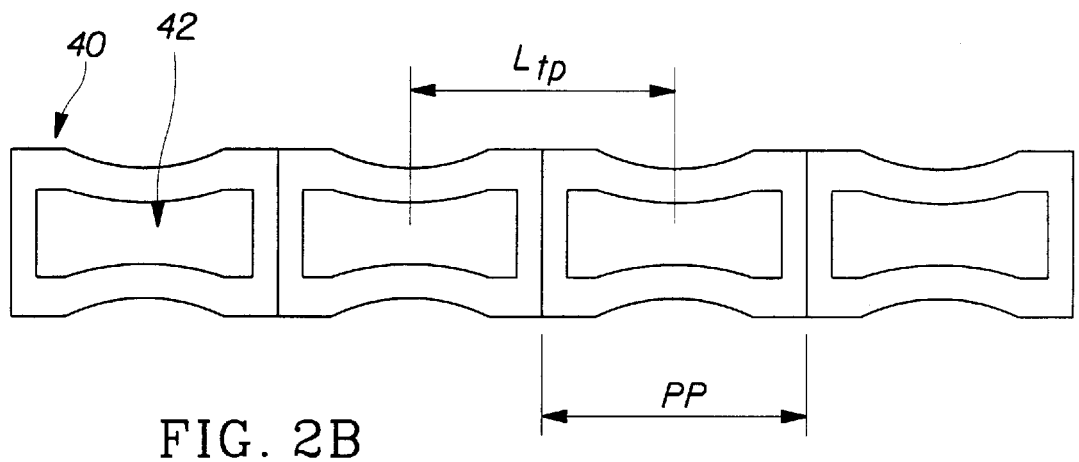
FIG. 2B is a top view of a diaper product web including a representation of the diaper core area.

In one embodiment, the target web comprises that part of the diaper chassis itself that is generally continuously comprised of the core and topsheet assembly, prior to the attachment of the backsheet web. The target web is represented in FIGS. 2A and 2B as target web 40. The target web 40 contains target objects 42 consecutively but not equidistantly spaced thereupon at a target web pitch length, "Ltp". Target objects 42 may be the absorbent cores of the disposable diaper chassis. Ltp need not be identical to the product pitch length PP of the diaper product; in fact, the target web 40 will likely have small but significant variation in consecutive product pitch lengths PP due to climatic conditions during storage and transport, thermally induced creep, and the like. In addition, it is noted that the pitch length Lpp of the controlled web 30 may be either longer or shorter than Ltp.

It is noted that the target object position may be directly sensed or inferred from the use of an electronic strobe. One embodiment of the present invention uses an electronic strobe. This signal happens once per machine cycle at the same place in the machine cycle. For example, if the machine cycle is represented by 1000 counts, then the strobe may be arbitrarily set at 500 to 600 "on" and balance of cycle "off". The leading edge transition between "off" to "on" marks a machine time fixed position to which a graphic is registered. When the system is first started up, the operator inputs an offset value using an "advance/retard" button while examining the position of the controlled web graphic using an actual strobe light. Once the offset value is set, the registration system will target the controlled web graphic to the same point in the machine cycle.

Again referring to FIG. 2A, the controlled web 30 may comprise a continuous film material, for example, a breathable microporous polymer film, that is used as part of the diaper backsheet. The controlled web 30 has preprinted objects 22, consecutively but not equidistantly printed thereupon at a particular controlled web pitch length, "Lpp". Lpp is invariably something other (either longer or shorter) than both the product pitch length PP and the pitch length of the target web Ltp due to climatic conditions, thermally induced creep, and the like. An exemplary Lpp is shown in FIG. 2A. Preprinted objects 22 may be registered graphics that are colorful, high resolution designs that are appealing to the consumer, who is typically a care-giver to the wearer of the diaper, or who in other cases may actually be the wearer.

As noted above, in most cases, Ltp is not equal to Lpp; in fact, exact matches are highly improbable. This difference is a major source of the difficulties associated with proper phasing of the controlled web 30 and the target web 40. As can be most clearly seen in FIG. 2A, a pitch delta C (e.g., Ltp minus Lpp) usually exists and must be corrected in order to insure proper product phasing. It is additionally noted that the pitch delta C associated with Ltp and Lpp typically accumulates for each subsequent target object 42, and thus a greater amount of correction is generally needed. This error accumulation of pitch delta is represented in FIG. 2A as C, C2, C3, C4.

The corrections of pitch delta C, C2, etc. associated with the registration system of the present invention may not actually be necessary for product functionality; however, they are critically important for consumer acceptance of the diaper products produced. And, in some cases, children wearing a disposable article herein that has an improperly phased graphic, e.g., an animal with its head cut off, may be upset.

Figure 3:
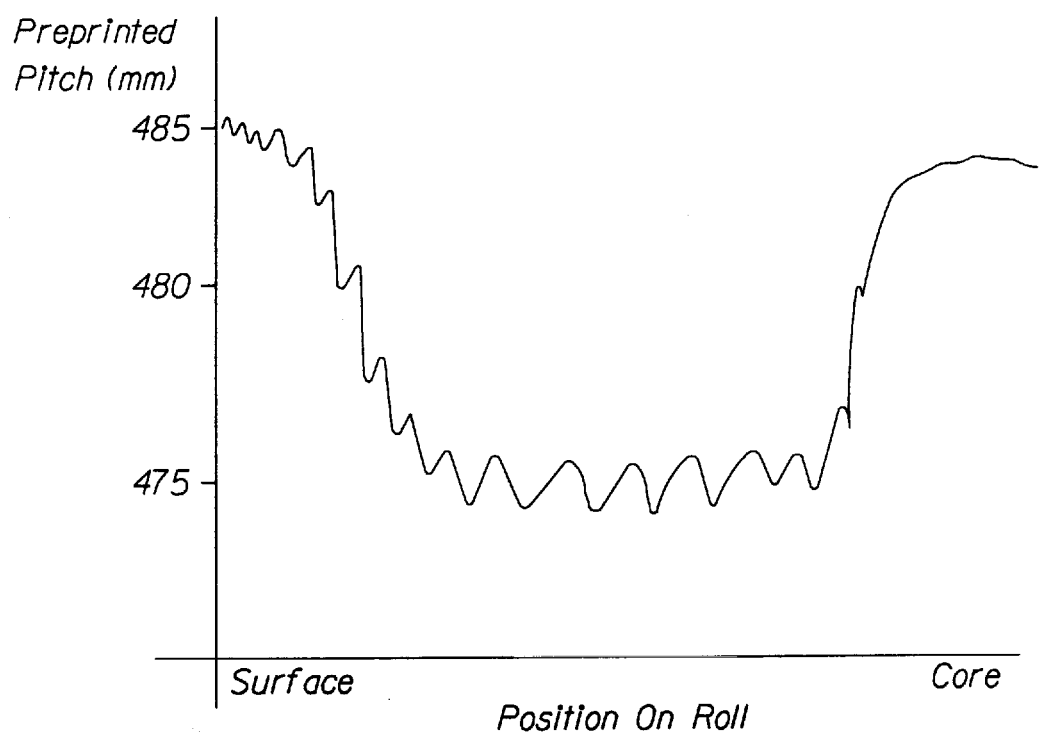
FIG. 3 is a graphical representation of the pitch length variation typically experienced by preprinted microporous materials that have been subjected to typical conditions of winding and warehouse storage.

FIG. 3 illustrates the instabilities in controlled web pitch length Lpp that may arise due to the inherent thermal instability of the microporous polymer films of the present invention. Such thermal instability leads to differential shrinkage of the microporous film, and significant variations in Lpp frequently result. Referring to FIG. 3, the position along a wound roll (i.e., a continuous, controlled web 30) of microporous polymer film that has been preprinted with registered graphics is represented on the X axis. The start of the roll is indicated at the origin of the axes, while moving to the right along the X axis indicates moving toward the core of the roll, corresponding to unwinding the roll.

On the Y axis, preprinted pitch length Lpp is represented in millimeters. As can be seen, differences in preprinted pitch lengths Lpp of up to about 10 mm may be seen between various locations on the same web of material.

The registration system of the present invention is thus designed to overcome the phasing problems associated with combining the target web 40 and the controlled web 30 where Ltp is not equal to Lpp, where Lpp is inherently variable, and where both webs are simultaneously and continuously fed to a combining operation. The process has the ability to on-goingly adjust the pitch length of the controlled web 30 as delivered to match or to more closely approximate that of the target web 40. In addition, the system of the present invention makes such correction in a gentle, non-abrupt and gradual fashion so as to account for the delicate nature of the web, which may be a microporous polymer film, without damaging it. Alternatively, if conventional higher strength webs are used, the system is capable of making more rapid and abrupt adjustments that may not be acceptable with the microporous polymer films.

As described more fully below, this is accomplished by the use of web tension transients to change the preprinted pitch length Lpp of the preprinted objects on the controlled web 30. Changing the tension in a web causes a change in the pitch length of the web. Thus, more tension stretches the material of controlled web 30, causing the pitch length Lpp to increase, while less tension relaxes the controlled web 30, causing the pitch length Lpp to decrease. The absolute tension in the controlled web 30 should not approach zero tension, as control of the controlled web 30 would be lost. Conversely, more or less web may be metered to the process, which also changes the level of tension in the web.

The system of the present invention thus introduces small tension transients, which provides on-going correction. This serves to maintain the integrity of the delicate, mechanically unstable polymer films that are useful for disposable absorbent articles herein. It also serves to correct the phase relationships of objects on the each incoming web in increments that are too small to be detected by the web handling process, which means that there is little possibility for the amount of error to become large enough to trigger the shut-down functions of the web handling process. In addition, it allows for manufacture of consecutive products that may have insignificant differences in the locations of the graphic objects on each product.

Any control algorithm that creates such small on-going transients is useful herein. The control system prepares small transient corrections in a timely fashion that intervene in the control of incoming web handling drives to prevent mismatches between the positions of the target object and the preprinted object from drifting out of the zone that the consumer would find acceptable. Exemplary control algorithms herein include manual control, a control algorithm based on statistical process control, or a PID control system.

It is believed that control systems relying on statistical analysis of past history such as running average are simply too sluggish to stay ahead of the significant variation observed in the position of graphics on the in-running controlled web 30. To avoid the complexity of controlling multiple drives to position the graphic, a preferred embodiment herein is a PID control algorithm which controls the feed rate of the controlled web 30 only as necessary to minimize the strobed distance between a fixed position of converter machine time with user-set offset and the sensed mark. If the space between the sensed marks of the controlled web 30 (Lpp), is longer than the target pitch length Ltp, more web 30 is fed to the process, reducing the web tension and allowing the space between graphics to contract. Conversely, if the space between the sensed marks of the controlled web 30 is too short, less web is fed, causing an increase in web tension causing the space between marks to increase. In this way, not only is the pitch of the web brought close to the pitch of the product, but the position of the graphic is brought close to the target position.

To determine the position of the preprinted objects on controlled webs various detectors/scanners may be used. For example, to determine the position of the color graphic on the incoming controlled web 30, a sensor is selected which detects differences between light passing through the web via different printed colors. The color of the target web object, the position of the target web object relative to other objects of the same color, and the size of the target object combine to create the means for generating a clean signal whose position is strobed once per machine cycle.

Alternative means of establishing position of preprinted objects include: 1) sensing a visible timing mark on a part of the web that is later removed by the process; 2) sensing a normally invisible to the human eye registration mark which may or may not remain a part of a final article or product; or 3) using a grid of sensors to look for a recognized pattern of light diffusion.

The invisible preprinted objects may be detected, for example, if they can fluoresce. Fluorescence is the process whereby light is absorbed by a substance, called a fluorophore, at one wave length and then re-emitted at a longer wave length. It should be noted that any electromagnetic waves of any length may be used for detecting the wave-emitting preprinted objects, however, a preferred wave length spectrum for detecting invisible marks on disposable absorbent articles is the infrared (IR) region of the electromagnetic spectrum including wave lengths from about 700 nm to about 2,500 nm, and a more preferred wave length spectrum is the near infrared (NIR) region including wave lengths generally from about 700 nm to about 1,100 nm. Another invisible wave length spectrum which may be used for detecting invisible marks is the ultraviolet (UV) region including wave lengths from about 1 nm to about 400 nm. (The visible region of the electromagnetic spectrum is located between the IR and UV regions and includes wave lengths from about 400 nm to about 700 nm.) The NIR mark is preferred over the UV mark in some instances because the UV mark may fluoresce or "glow in dark" under certain conditions of home lighting because it may fluoresce longer than UV waves and thereby becomes visible to consumers. The NIR marks may include inks containing substances that fluoresce primarily in the NIR region of the electromagnetic spectrum, as, for example, are the inks described in U.S. Pat.

No. 4,540,595 entitled "Article Identification Material and Method and Apparatus For Using It," issued to Acitelli et al. on Sep. 10, 1985 and U.S. Pat. No. 5,665,151 entitled "Method For Making Articles With And Detecting Water Based Inks Containing Near Infrared Fluorophores," issued to Escano et al. on Sep. 9, 1997, each of the patents is incorporated herein by reference. The NIR marks may be detected, for example, by using Smarteye® STEALTH sensor made by TRI-TRONICS® Co., Inc. of Tampa, Fla.

Figure 6:
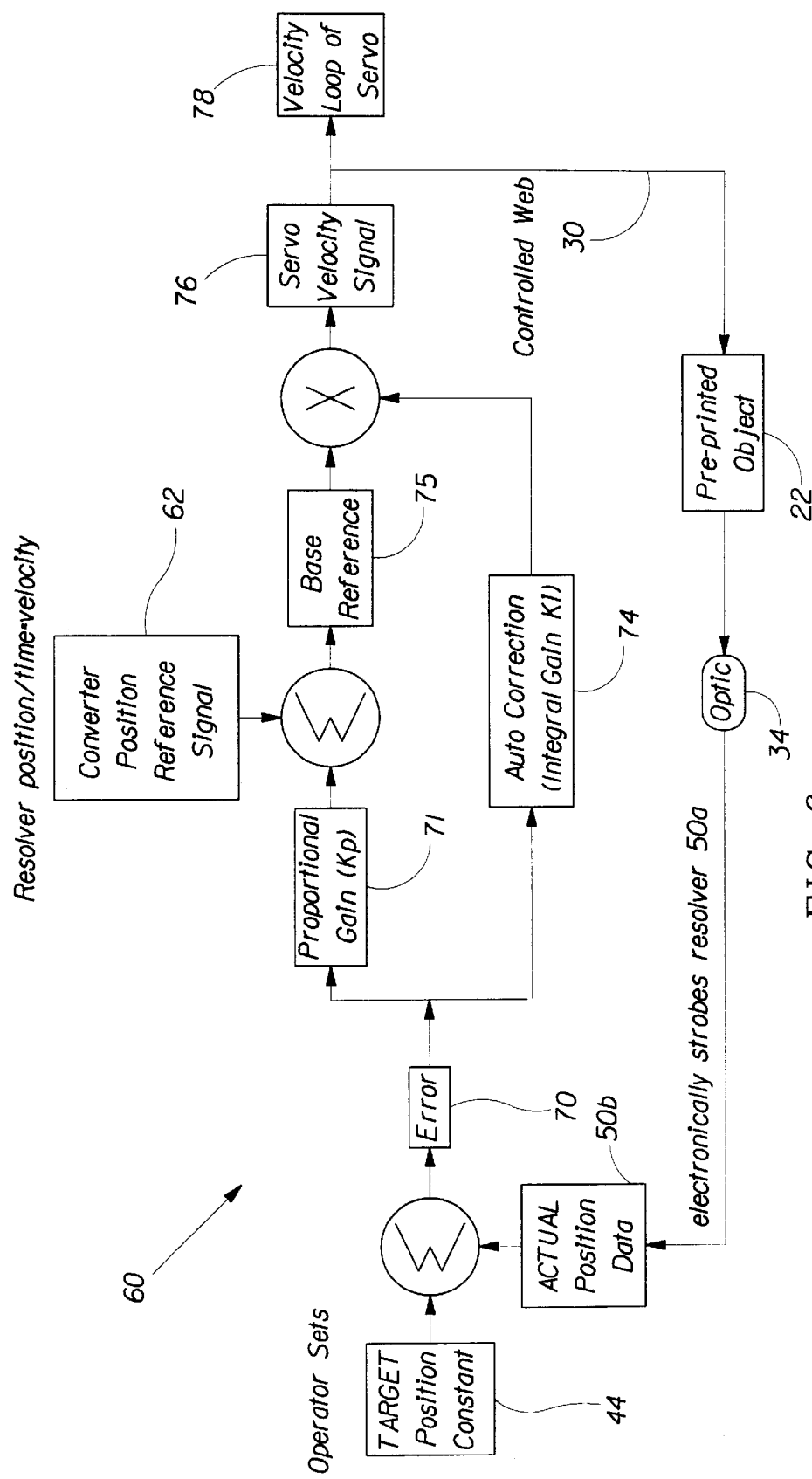
FIG. 6 is a schematic diagram showing a preferred registration control system of the present invention.

The PID control system shown in FIG. 6 seeks to minimize the error distance which is observed once per product. The proportional gain (Kp) 71 sends a correction signal to the controlled web feed drive that is proportional to the size of the error. The integral gain factor (Ki) 74 is set to eliminate the steady state offset typical of purely proportional control. While a differential gain factor may also be used, it is believed that best results are obtained by setting this equal to zero. It is observed in FIG. 6 that the error signal trims the operation of the feed drive which is typically running at "gear ratio" relative to rate of product production. Although speed and position may vary, on average one preprinted object must be processed per target product.

The registration system of the present invention preferably adjusts the pitch Lpp of the controlled web 30 by on-goingly adjusting the tension in the controlled web 30. The Lpp is adjusted to "Lc", which is used herein to mean "length at combining." Lc is equal or approximately equal to Ltp, i.e., the pitch length of the controlled web 30 is made approximately equal to that of the target web 40 so that the preprinted object, for example, graphic 22, can be positioned in the correct phase relationship to the product. This tension acts through the web modulus, Ew, of the controlled web 30, according to the following equation:

$$Lc=(1+\epsilon) \times Lpp=(1+T/Ew) \times Lpp, \text{ where}$$

$\epsilon$=strain;

T=controlled web tension; and

Ew=web modulus of controlled web.

The foregoing equation acts for all webs being combined together. Thus in the case of two webs:

$$Lc1=(1+T1/Ew1) \times Lpp1 \text{ and } Lc2=(1+T2/Ew2) \times Lpp2.$$

As noted above, at the point of registered combining under steady state conditions, Ltp is equal to Lc. Thus, the ratio of the relaxed lengths combined at any time is given by the equation:

$$Lc1/Lc2=(1+T2/Ew2)/(1+T1/Ew1).$$

The tension variables T as well as the modulus variables Ew each have a range of variation, so the ratio of the Lc values will always vary somewhat from unity. The difference between the Lc ratio and unity is referred to herein as "puckering":

$$\text{Puckering \%}=(Lc1/Lc2-1) \times 100.$$

The puckering value can assume positive or negative values depending which web has the least relaxed length. After the finished product is cut apart, the combined web is pulled to the length of the incoming web with the least relaxed length. This causes the other web to "pucker." Above a certain tolerance level, puckering has a noticeable impact on the appearance of the product. For a diaper backsheet formed from a nonwoven material and a polymer film preprinted with graphic designs, puckering levels up to about ±2%, while noticeable, are generally not perceived as distorting the appearance of the product. The puckering levels of up to ±2% can be beneficial to provide desired matt finishes, textural, and tactile properties of the finished product. However, puckering levels can be also outside of the above ±2%, for example, when it is desired to create high loft web structures and/or to conceal from the eye of the consumer items inside the product (such as, for example, glue beads, unbleached pulp in the absorbent core, any urine and/or fecal sensory devices visible inside the product, any imperfections, and the like). In such cases, the puckering levels can be any desirable number permitted by material properties of the web such as, for example, elastic, tensile strength, poison ratio, and the like. In some instances, the puckering levels can be within the elastic properties of the web to ensure that the stretched web contracts back after combining and cutting into individual products. In other instances, the puckering levels can be outside the range of elasticity of the web, in the plastic area of the material properties (but preferably within the limits of the tensile strength) to create a desired appearance, including texture, tactile, light-reflecting, and other material properties. Accordingly, the puckering levels can be ±2% and greater, such as ±5%, ±10%, ±20%, ±50%, or even greater.

Alternatively, different puckering levels can intentionally be created, or puckering may otherwise be controlled to create materials with different tactile feels as desired. Note that even below ±2% that puckering can be controlled and located on the product according to the present invention to minimize its impact on product appearance. To do this, the laminated material furthest away from the consumer is overfed and pulled back, thus hiding the puckering from the consumer.

The present invention has the capability of registering controlled webs having pitch lengths that are not uniform, and which can be either longer or shorter than the machine product pitch length. The ability to register materials with pitch lengths longer than the product under production allows the designer of such a product to tailor the surface texture of the product. This is demonstrated in FIGS. 4A and 4B, where two materials are laminated together by passing through a nip point. The material which is longer than the finished product pitch is pulled back by the other material. By making the layer of the laminate that is furthest away from the eye of the consumer the material that is pulled back, the impact of the registration process on the texture of the finished product is mitigated.

Figure 4A:
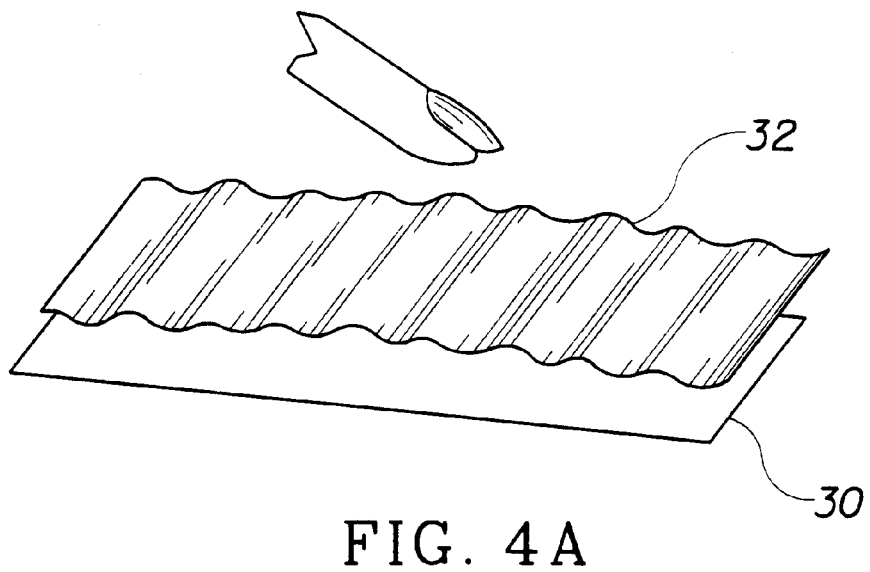
FIGS. 4A and 4B are perspective views of portions of preferred embodiments of laminates of microporous material and nonwoven material, illustrating the impact of running the microporous material at a pitch length different from that of the nonwoven material.

In FIG. 4A, the pitch length of the nonwoven web 32 (Ltp) which may form a portion of the diaper backsheet is longer than the pitch length (Lpp) of the polymer film (controlled web) 30. In this case, after the final cut that separates the consecutive diaper products, the polymer film pulls back the nonwoven material. This creates a roughened texture on the exposed surface of the laminate which the consumer can see and feel.

Figure 4B:
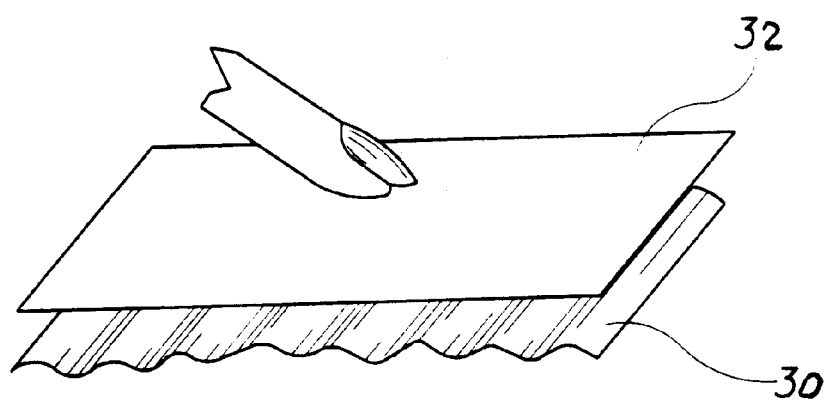

FIG. 4B shows the surface texture impact of the pitch lengths (Lpp) of the polymer film (controlled web) 30 longer than the pitch length (Ltp) of the nonwoven material web 32. In this case, the nonwoven material pulls back the polymer film material after the final cut. Thus, the impact of the unequal combining is manifested on the inside of the product and is hidden from the eye of the consumer. Thus, it is generally preferable to overfeed the controlled web of polymer film material so that the consumer does not see or feel the roughened texture.

The nonwoven material 32 may be fed into the system as an independent web having phased objects with variable pitch length. In such a case, the nonwoven web and preferably the controlled web are phased as described herein, and combined; then the combination laminate material is phased and combined to the target web (diaper product web) as described herein.

Assuming that a puckering tolerance level of up to about ±2% is acceptable, the available adjustment rate for registered graphics is limited. It is important to design the registered printing such that a reasonable tolerance of graphic position is accommodated. The graphic position tolerance should be greater than or equal to the web to web position shift typically seen at the time of web splicing; that is, at the time that a subsequent roll of preprinted web is supplied to the web combining process at the time that the previous roll is used up by the process. The roll to roll error is different and generally greater that the normal variation within a single roll. Thus, if random splicing were used, phasing corrections of up to 180 degrees (half of a full length) would sometimes be necessary. During such times, all product produced would need to be scrapped. The splice tolerances of the present invention are controlled in concert with the tolerances of preprinted object position to reduce splice time rejected product to ideally zero (other than rejection of the splice tape itself).

The selection of the raw material to be used for the backsheet, i.e., the controlled web 30, may be constrained by both the product design and the registration system of the present invention. The key parameters that may be unique to registered graphics are impacted by the needs of product functionality. For diaper backsheet, a preferred material is a breathable microporous polymer film. A preferred microporous polymer film is formed from a mixture of polyethylene and calcium carbonate, and titanium dioxide if needed to increase the white appearance of the film, since whiteness is a film characteristic that is necessary for widespread consumer acceptance. More preferably, the microporous polymer film has high thermal stability characteristics in order to support the printing of high resolution color graphics thereon. Preferably the film meets a maximum of ±1% repeat pitch variation, i.e., mismatch, but more typically ±2% is likely to be seen. It is believed that puckering ratios ranging from about 0.97 to about 1.015 may successfully be provided using this system, making it possible to handle films with an even wider range of pre-printed pitch length variation.

Other preferred characteristics of the microporous polymer film that are important in assuring good processing with the registration system of the present invention include: web modulus (preferably from about 4000 to about 13,000); coefficient of friction (preferably high enough so that the system metering nips can act on the web with a sustainable level of web tension); and thermal enthalpy (preferably high enough to have sufficient heat resistance during hot melt glue lamination, but not increased to the point that the stiffness of the film increases to the point of discomfort for the wearer).

The process of combining the two webs 30 and 40 is schematically represented in FIG. 5. The controlled web 30 is initially fed at a velocity Vo. The target web 40 is fed to the combining stage 50 at a velocity Vt. Detection of the position of a preprinted object (e.g., graphic 22) of the control web 30 moving in the machine direction MD occurs at preprinted object detection stage 33 via an optic 34 which electronically strobes a resolver 50a providing actual position data 50b of the preprinted object 22 (see FIG. 6). Similarly, detection of a target object (e.g., diaper core 42) on the target web 40 moving also in the machine direction MD, occurs at the product detection stage 45, preferably manually by an operator setting the target position constant 44 (see FIG. 6) which is the target position of the preprinted object 22 for combining the preprinted object (graphic 22) with the corresponding target object (core 42), or alternatively, via any suitable optic working in combination with resolver 50a sensing the target object 22 on the target web 40 (i.e., automatically).

As previously noted, the process control dilemma that the registration system of the present invention must correct is two-fold.

First, pitch mismatch must be corrected. There is a difference in pitch between the online made web (target web 40) and the offline made web (control web 30). This difference in pitch is shown in FIGS. 2a and 5, as the difference between Ltp and Lpp, where Ltp−Lpp=pitch delta C). As described in connection with FIG. 2a, this pitch delta C accumulates as the number of products accumulates. Thus, for the first product, the pitch delta is about C; for the second product, the pitch delta is about C2; for the third product, the pitch delta is about C3, and so on.

Second, phase correction is needed. Phase error may be caused when a transient change occurs in the controlled web 30 via a control web splice or some phase upset in the position of the preprinted object 22 in relationship to the target object 42.

In a preferred PID control system of the present invention, error signal 70, see FIG. 6, is generated based upon recording of position of incoming timing mark by resolver strobe. This error signal is transformed into a correction signal via a PID algorithm. In a preferred algorithm, integral gain is used to attenuate steady state error, and differential gain is preferably set at zero. This correction signal forces a programmable drive or differential correction shaft to speed up or slow down the axis driving the controlled web 30 at a metering point 30b. Thus, Vo is adjusted to Vc (see FIG. 5) by gain factors 71 and 74, see FIG. 6, to maintain the position of the preprinted object graphic 22 and the target object core 42, by changing flow rate of the controlled web 30.

Referring to FIG. 6, a preferred registration control system 60 is shown. The main reference signal is provided by the resolver 50a and is referred to as the converter position reference signal 62. The converter position reference signal 62 is the resolver change in position over time, i.e., a velocity reference signal (preferably one revolution of the resolver per target object 42). This signal 62 is equal to the pitch length of the product times the converter rate. The registration control system 60 provides a trim correction factor, which is typically a small percentage of the servo velocity reference signal 76, to the converter position reference signal 62, based on the pitch mismatch and phase correction described above, by automatically calculating an error signal 70 and adjusting the servo system velocity via the velocity loop 78, to change the flow rate of the control web 30. This is accomplished by the controlled web 30 preprinted object 22 being sensed by optic 34 that electronically strobes resolver 50a providing actual position data 50b (feedback), and comparing it to the fixed target position constant 44. This error signal 70 is manipulated to maintain registration due to pitch mismatch and phase correction.

The pitch mismatch aspect of the control dilemma is used to limit the accumulating offset, i.e., pitch delta C, C2, C3, and so on. Integral gain Ki (auto correction 74) is multiplied by the base reference signal 75 to yield a servo velocity signal 76 to the velocity loop of the servo drive 78, thus matching the pitch of the controlled web 30 to the target web 40. The proportional gain Kp 71 is needed to stabilize the system and provide enough gain to maintain the target position 44.

The phase correction aspect of the control dilemma, i.e., the process control issue, is used to phase the system for several reasons. First, initial set-up of the registration system 60 online requires phase correction. When the registration system 60 is first started up, the position of the preprinted object 22 assumes an arbitrary but controlled position relative to that of the target object 42. This arbitrary position may be out of phase, requiring the operator to change the fixed target position constant 44 to initially set the preprinted object 22 to the target object 42 (from this time on no additional manual intervention is needed). Proportional gain 71 is needed to drive the system 60 to new setpoint, target constant 44. The error signal 70 is multiplied by a proportional gain factor 71 and then added to a converter position reference 50a to generate a base reference signal 75.

In addition, web splicing of control web 30 causes a phase error, requiring phase correction. Proportional gain 71 is needed to drive the system to the set point target constant 44.

Previous design efforts targeting registered graphics have been based upon separate control systems for incoming graphics pitch length correction and phase position control. However, the system of the present invention incorporates simultaneous correction based upon the relationship between pitch length and the velocity. It will be understood by those of skill in the art that position has an integral relationship to velocity and can therefore be controlled using the same system that controls velocity.

Disposable diaper products typically include a topsheet material, an absorbent core, and a backsheet material. The topsheet material is located to be placed facing the body or nearest the body when the diaper is worn and is generally provided with a liquid permeable region so that body exudates can flow through the topsheet to the absorbent core, where they are contained. The backsheet material, which is placed away from the body during wear, is typically liquid impermeable so that outer clothing or other articles such as bedsheets are not wetted by the body exudates. Such an exemplary diaper is disclosed in, for example, Buell U.S. Pat. No. 5,569,234, directed to a "Disposable Pull-on Pant".

In addition to the basic topsheet, core, and backsheet components, it will be understood by those of skill in the art that many other features for disposable absorbent articles are within the scope of the present invention. For example, barrier cuffs as described in Lawson and Dragoo U.S. Pat. Nos. 4,695,278 and 4,795,454 are a desirable feature for disposable absorbent articles. In addition, skin care type topsheets that are provided with lotion thereon for the purpose of reducing skin irritation and chafing are a desirable feature herein.

Figure 7:
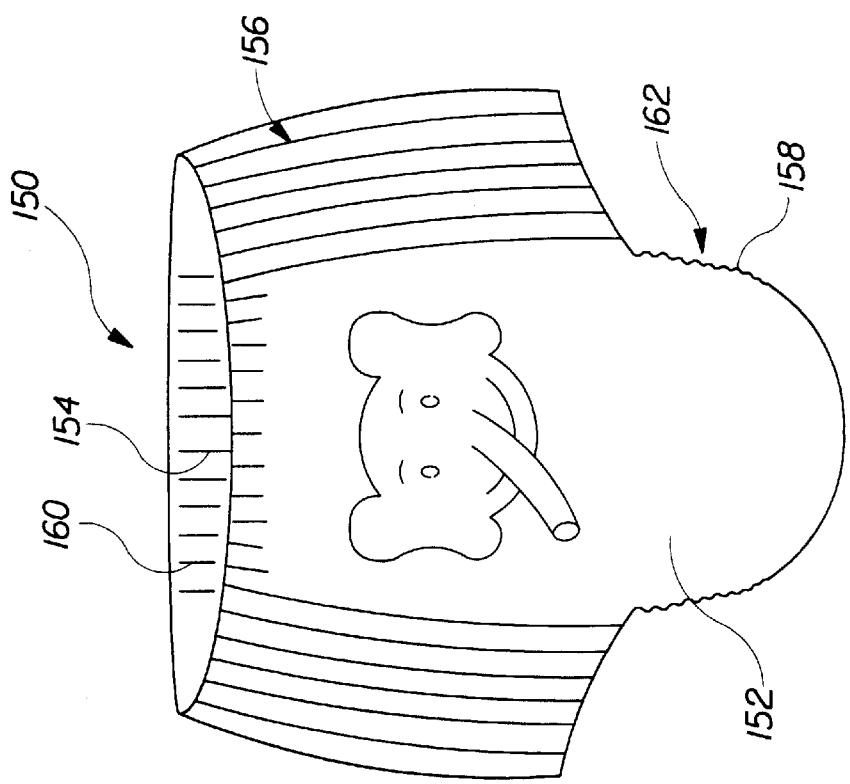
FIG. 7 is a front view of a preferred embodiment of a disposable absorbent article having registered graphics.

Referring to FIG. 7, there is shown an exemplary disposable pull-on diaper 150, which is generally pulled onto the body of the wearer by inserting the legs into the leg openings 162 and pulling the article up over the waist. Generally, "pull-on diaper" refers to pull-on garments worn by small children and other incontinent individuals to absorb and contain body exudates. It should be understood that other pull-on garments such as training pants, incontinent briefs, feminine briefs, feminine hygiene garments or panties, and like, are included herein.

Figure 8:
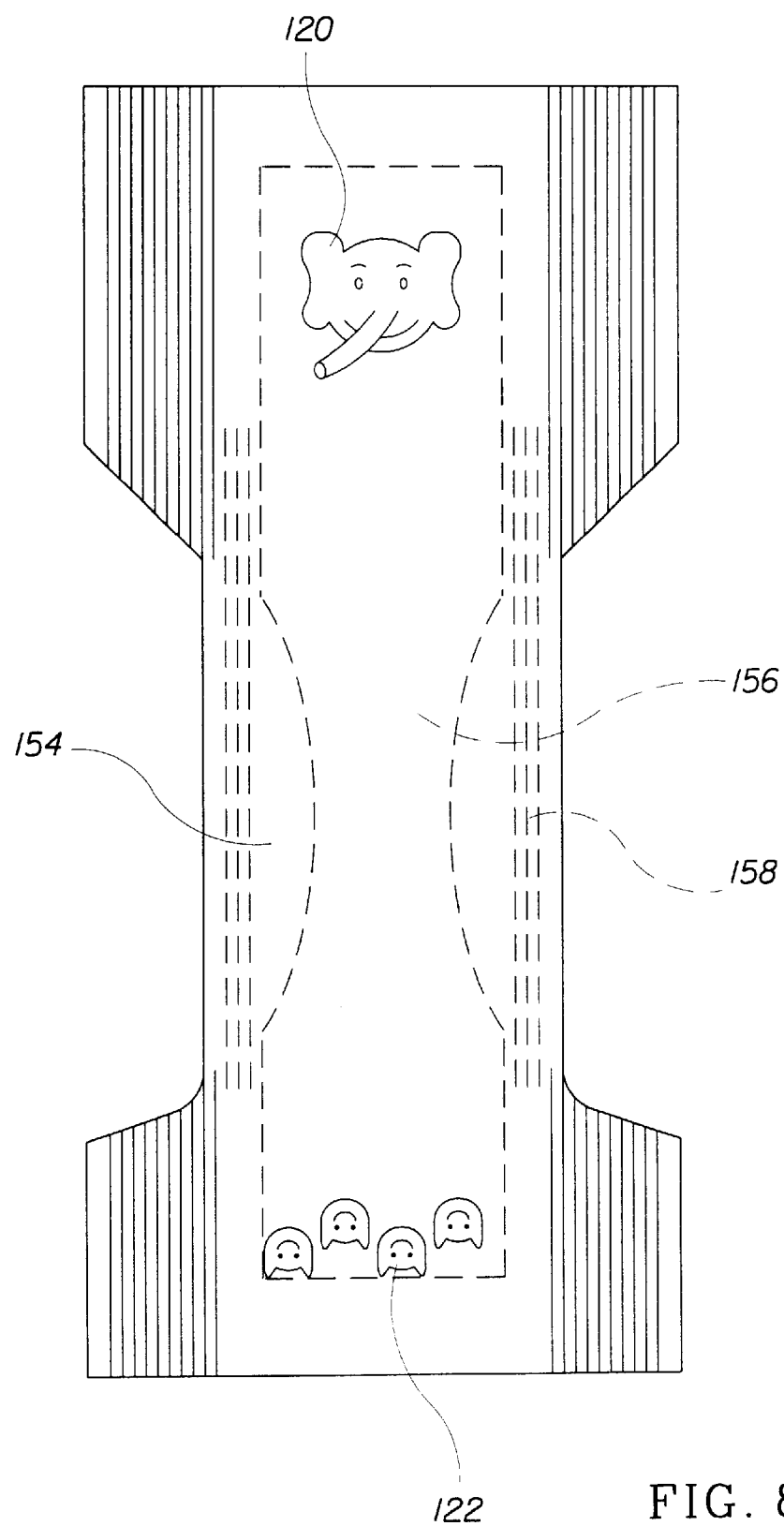
FIG. 8 is a simplified plan view of another preferred embodiment of a disposable absorbent article having registered graphics.

Referring to FIGS. 7 and 8, the diaper 150 is generally comprised of a backsheet 152, a topsheet 154 and an absorbent layer 156 (shown in dashed lines in FIG. 8) located between the backsheet 152 and the topsheet 154. The backsheet 154 is the surface which faces away from the wearer's body, while the topsheet 152 is the surface which faces toward the wearer's body. In one embodiment of the present invention, the backsheet 152 is comprised of at least a microporous polymer film printed with registered graphics, e.g., 120, 122, as described herein. The backsheet 152 may further comprise a layer of nonwoven material (see reference numeral 32, FIGS. 4A, B) laminated or otherwise secured to the microporous film layer, in which case there is provided a more cloth-like and garment-like feel. In such a case, the nonwoven web may be fed to the web handling process as a continuous incoming web and may be combined in a desired relationship with the controlled web 30 and the target web 40.

In the case of a laminated nonwoven backsheet, it is desirable that the surface texture of the non-woven not be impacted by a laminated sublayer, e.g. a microporous polymer film sublayer, which pulls it back and causes it to "pucker." It is more desirable that any puckering that is required for the operation of a registration system be limited to the underlying polymer material, which is neither seen nor felt by the user of the product, see FIG. 4B. The system of the present invention can be used in cases where the pitch length Lpp of the microporous film web (controlled web 30) may be longer or shorter than that of the product, Ltp. Overfeeding the target web may lead to superior surface texture. After the final cut, when Lpp is less than Ltp, the film material pulls back the nonwoven material that forms part of the product. This creates a roughened texture of the exposed surface of the laminates where the consumer can see and feel. This, when Lpp is greater than Ltp, the impact of the unequal combining upon which the registration systems depends is hidden from the consumer. In general, Lc should be greater than both Lpp and Ltp, to avoid the possibility of a zero-tension situation.

Elastically extensible side panels 156 are provided to ensure more comfortable and contouring fit by initially conformably fitting the pull-on diaper 150 to the wearer and sustaining this fit throughout the time of wear well past when it has been loaded with exudates. Leg elastics 158 and waist elastic region 160 are also provided to enhance the fit around the legs and waist, respectively.

FIG. 7 shows the front view of the diaper 150 with an exemplary graphic 120 positioned in about the upper region of the backsheet, on the front side of the diaper 150. In FIG. 8, there is shown a simplified plan view of an embodiment of a disposable absorbent article in its flat, uncontracted state prior to formation. In this embodiment, graphic 120 is shown in the back region of the diaper with graphics 122 additionally shown in the front region of the diaper.

It is understood that the examples and embodiments described herein are for illustrative purposes only and that various modifications or changes in light thereof will be suggested to one of skill in the art without departing from the scope of the present invention.

What is claimed is:

1. A registration method far phasing simultaneously advancing webs of material having variable pitch lengths, the method comprising the steps of:

a. providing a continuous target web containing consecutively spaced target objects along a path at a first velocity, the target web having a target web pitch length between consecutive target objects;

b. providing a continuous controlled web of material preprinted with consecutively spaced preprinted objects along a path at a second velocity, the controlled web having controlled web pitch length between consecutive preprinted objects;

c. detecting the preprinted objects of the controlled web by sensing by an optic that electronically strobes a resolver providing actual position data;

d. generating an error signal based upon the detection of the preprinted objects of the controlled web and comparing to a fixed target position constant;

e. adjusting the controlled web pitch length such that the controlled web pitch length is approximately equal to the target web pitch length to maintain registration due to pitch mismatch; and f. adjusting the second velocity such that the preprinted objects are shifted toward the target objects a the target web, wherein the controlled web pitch length is greater than the target itch length to pucker the controlled web to provide desired visual and tactile properties to a finished product.

2. The registration method of claim 1 wherein the controlled web has a puckering level of +/−1%.

3. The registration method of claim 1 wherein the controlled web has a puckering level of +/−5%.

4. The registration method of claim 1 wherein the controlled web has a puckering level of +/−10%.

5. The registration method of claim 1 wherein the controlled web has a puckering level of +/−20%.

6. The registration method of claim 1 wherein the controlled web has a puckering level of +/−50%.

7. The registration method of claim 1 wherein the preprinted object includes an element of a disposable absorbent article.

8. The registration method of claim 1 wherein the preprinted object includes a registration mark.

9. The registration method of claim 1 wherein the preprinted object is normally invisible to the human eye.

10. The registration method of claim 1 wherein the preprinted object includes a fluorophore.

11. The registration method of claim 10 wherein the fluorophore is capable of emitting electromagnetic wavelengths in the infrared (IR) spectrum from about 700 nm to about 1,500 nm.

12. The registration method of claim 10 wherein the fluorophore is capable of emitting electromagnetic wavelengths in the near infrared (NIR) spectrum from about 700 nm to about 1,100 nm.

13. The registration method of claim 10 wherein the preprinted object includes a registered graphic.

* * * * *

UNITED STATES PATENT AND TRADEMARK OFFICE
CERTIFICATE OF CORRECTION

PATENT NO. : 6,764,563 B2
DATED : July 20, 2004
INVENTOR(S) : Henry et al.

It is certified that error appears in the above-identified patent and that said Letters Patent is hereby corrected as shown below:

Column 14,
Line 56, delete "far" and insert -- for --.

Column 15,
Line 12, delete "a" and insert -- on --.
Line 14, delete "itch" and insert -- pitch --.
Line 18, delete "1%" and insert -- 2% --.

Column 16,
Line 15, delete "1,500" and insert -- 2,500 --.

Signed and Sealed this

Seventh Day of March, 2006

JON W. DUDAS
*Director of the United States Patent and Trademark Office*